(12) United States Patent
Suzuki et al.

(10) Patent No.: US 8,034,193 B2
(45) Date of Patent: Oct. 11, 2011

(54) ENDOSCOPE CLEANING/DISINFECTING APPARATUS

(75) Inventors: Eiri Suzuki, Sagamihara (JP); Toshiaki Noguchi, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 1028 days.

(21) Appl. No.: 11/918,701

(22) PCT Filed: Apr. 20, 2006

(86) PCT No.: PCT/JP2006/308347
§ 371 (c)(1),
(2), (4) Date: Oct. 17, 2007

(87) PCT Pub. No.: WO2006/115177
PCT Pub. Date: Nov. 2, 2006

(65) Prior Publication Data
US 2009/0065034 A1    Mar. 12, 2009

(30) Foreign Application Priority Data

Apr. 25, 2005 (JP) ................................. 2005-127011

(51) Int. Cl.
*B08B 3/04* (2006.01)
(52) U.S. Cl. ................ 134/166 C; 134/168 C; 134/170; 422/300
(58) Field of Classification Search .............. 134/166 C, 134/168 C, 170; 422/300
See application file for complete search history.

(56) References Cited

U.S. PATENT DOCUMENTS

| 5,627,584 | A  | * | 5/1997  | Nishikori et al. ............... 348/72 |
| 5,715,555 | A  | * | 2/1998  | Reber et al. ....................... 8/158 |
| 6,323,782 | B1 | * | 11/2001 | Stephens et al. ........... 340/10.31 |
| 2002/0073411 | A1 | * | 6/2002  | Tsunedomi et al. .......... 717/171 |
| 2002/0161460 | A1 |   | 10/2002 | Noguchi |
| 2004/0197248 | A1 | * | 10/2004 | Hasegawa et al. ............ 422/297 |
| 2005/0000553 | A1 | * | 1/2005  | Noguchi et al. ................ 134/84 |
| 2005/0148819 | A1 | * | 7/2005  | Noguchi et al. .............. 600/133 |

FOREIGN PATENT DOCUMENTS

| JP | 2002-263066 |   | 9/2002 |
| JP | 2002-272682 |   | 9/2002 |
| JP | 2004-174043 | * | 6/2004 |
| WO | WO 02/32468 |   | 4/2002 |

* cited by examiner

*Primary Examiner* — Frankie L Stinson
(74) *Attorney, Agent, or Firm* — Scully, Scott, Murphy & Presser, P.C.

(57) ABSTRACT

An endoscope cleaning/disinfecting apparatus 1 according to the prevent invention includes an apparatus body 2 including a cleaning tank 6 for storing an endoscope retaining tray 4 in which an endoscope 5 is stored, a top cover 3 provided to the apparatus body 2 and caused by a cover body opening/closing mechanism unit to rotationally move between an open-state stop position and a closed-state stop position, a wireless tag 14 provided to either one of the endoscope retaining tray 4 and the endoscope 5 stored in the endoscope retaining tray 4 and transmitting information for identifying the type of the endoscope 5, a wireless receiver unit 22 provided to the apparatus body 2 and receiving the information of the wireless tag 14, and a control unit 10 provided to the apparatus body 2 and determining whether or not to cause an opening movement of the top cover 3 on the basis of the information obtained by the wireless receiver unit 22 to thereby control the rotational movement by the cover body opening/closing mechanism unit. Accordingly, cleaning and disinfection of the used endoscope can be hygienically and effectively performed.

6 Claims, 8 Drawing Sheets

ENDOSCOPE CLEANING/DISINFECTING APPARATUS

TECHNICAL FIELD

The present invention relates to an endoscope cleaning/disinfecting apparatus for cleaning and disinfecting a used endoscope.

BACKGROUND ART

In an endoscope used for such purposes as examination and treatment in a body cavity, dirt adheres not only to the outer surface of an insertion section inserted into the body cavity, but also to respective tubes, such as an air/water supply tube provided inside the insertion section and a suction tube also serving as a forceps channel. Therefore, the endoscope is cleaned and disinfected after the use thereof.

For example, Japanese Unexamined Patent Application Publication No. 2002-263066 discloses an endoscope cleaning/disinfecting apparatus for cleaning and disinfecting an endoscope. According to the endoscope cleaning/disinfecting apparatus, in a cleaning process, a rinsing process, and a disinfection process, which form a cleaning and disinfection process, the properties of electrolyzed water used for the cleaning and disinfection are adjusted in accordance with the extent of dirt accumulated on the endoscope, without the need for a complicated operation.

In a conventional endoscope cleaning/disinfecting apparatus, so as to be able to clean and disinfect plural types of endoscopes, i.e., endoscopes different in, for example, length, thickness, and specification of the insertion section thereof, the size of a cleaning tank provided in the endoscope cleaning/disinfecting apparatus is adjusted to an endoscope of the largest size. Further, in a facility having an upper gastrointestinal endoscope and a lower gastrointestinal endoscope, in many cases, each of the endoscopes has been cleaned and disinfected by a special cleaning/disinfecting apparatus for the endoscope.

Furthermore, according to the conventional endoscope cleaning/disinfecting apparatus, in the cleaning and disinfection of an endoscope, an operator carries the used endoscope to the endoscope cleaning/disinfecting apparatus.

However, if the cleaning and disinfection is performed on an endoscope of the smallest size in the endoscope cleaning/disinfecting apparatus having the cleaning tank adjusted to the endoscope of the largest size as described above, the amounts of cleaner and disinfectant to be used, the cleaning and disinfection time, and so forth are set to be the same as those for the endoscope of the largest size. Thus, there arises a problem in that the cleaner and the disinfectant are consumed more than necessary for the small-sized endoscope, and that the cleaning and disinfection time is increased.

Further, in the facility having the upper gastrointestinal endoscope and the lower gastrointestinal endoscope, there is a risk of occurrence of an operational error, such as setting the upper gastrointestinal endoscope in the cleaning/disinfecting apparatus for the lower one due to carelessness of the operator.

Furthermore, it is conceivable that the operator grasps the used endoscope directly with a hand and carries the endoscope to the cleaning/disinfecting apparatus for the cleaning and disinfection of the endoscope. In such a case, to set the endoscope in the cleaning tank of the cleaning/disinfecting apparatus, there arises a need to grasp a cover body of the apparatus with the unclean hand to open the cover body of the apparatus or a need to operate open and close switches and so forth with the unclean hand. As a result, there arises a problem in that the hygiene of the cleaning/disinfecting apparatus is deteriorated. To solve the problem, it is conceivable to provide the endoscope cleaning/disinfecting apparatus with a foot pedal as well as a mechanism for performing opening and closing operations of the cover body of the apparatus. However, the operation of checking the position of the foot pedal to open or close the cover body may be found bothersome by a user.

The present invention has been made in light of the above-described problems. An object of the present invention is to provide an endoscope cleaning/disinfecting apparatus capable of hygienically and effectively cleaning and disinfecting a used endoscope.

DISCLOSURE OF INVENTION

Means for Solving the Problems

An endoscope cleaning/disinfecting apparatus according to the present invention includes an apparatus body including a cleaning tank for storing an endoscope retaining tray in which an endoscope is stored, a cover body provided to the apparatus body and caused by a cover body opening/closing mechanism unit to rotationally move between an open-state stop position and a closed-state stop position, a wireless transmitter unit provided to either one of the endoscope retaining tray and the endoscope stored in the endoscope retaining tray and transmitting information for identifying the type of the endoscope, a wireless receiver unit provided to the apparatus body and receiving the information of the wireless transmitter unit, and a control unit provided to the apparatus body and determining whether or not to cause an opening movement of the cover body on the basis of the information obtained by the wireless receiver unit to thereby control the rotational movement by the cover body opening/closing mechanism unit.

According to the configuration of the endoscope cleaning/disinfecting apparatus, the endoscope is carried, stored in the endoscope retaining tray. Accordingly, the hands are prevented from becoming unclean during the carriage of the endoscope, and the cleaning/disinfecting apparatus is prevented from becoming unsanitary. Further, from the information sent from the wireless transmitter unit, the control unit determines whether or not to cause the opening movement of the cover body, to thereby control the rotational movement by the cover body opening/closing mechanism unit. Accordingly, an operational error, such as setting an upper gastrointestinal endoscope in a cleaning/disinfecting apparatus for a lower one, is prevented. Further, a user is released from opening and closing operations of the cover body, which have been bothersome operations for the user.

BEST MODE FOR CARRYING OUT THE INVENTION

An embodiment of the present invention will be described below with reference to the drawings.

Figure 1:
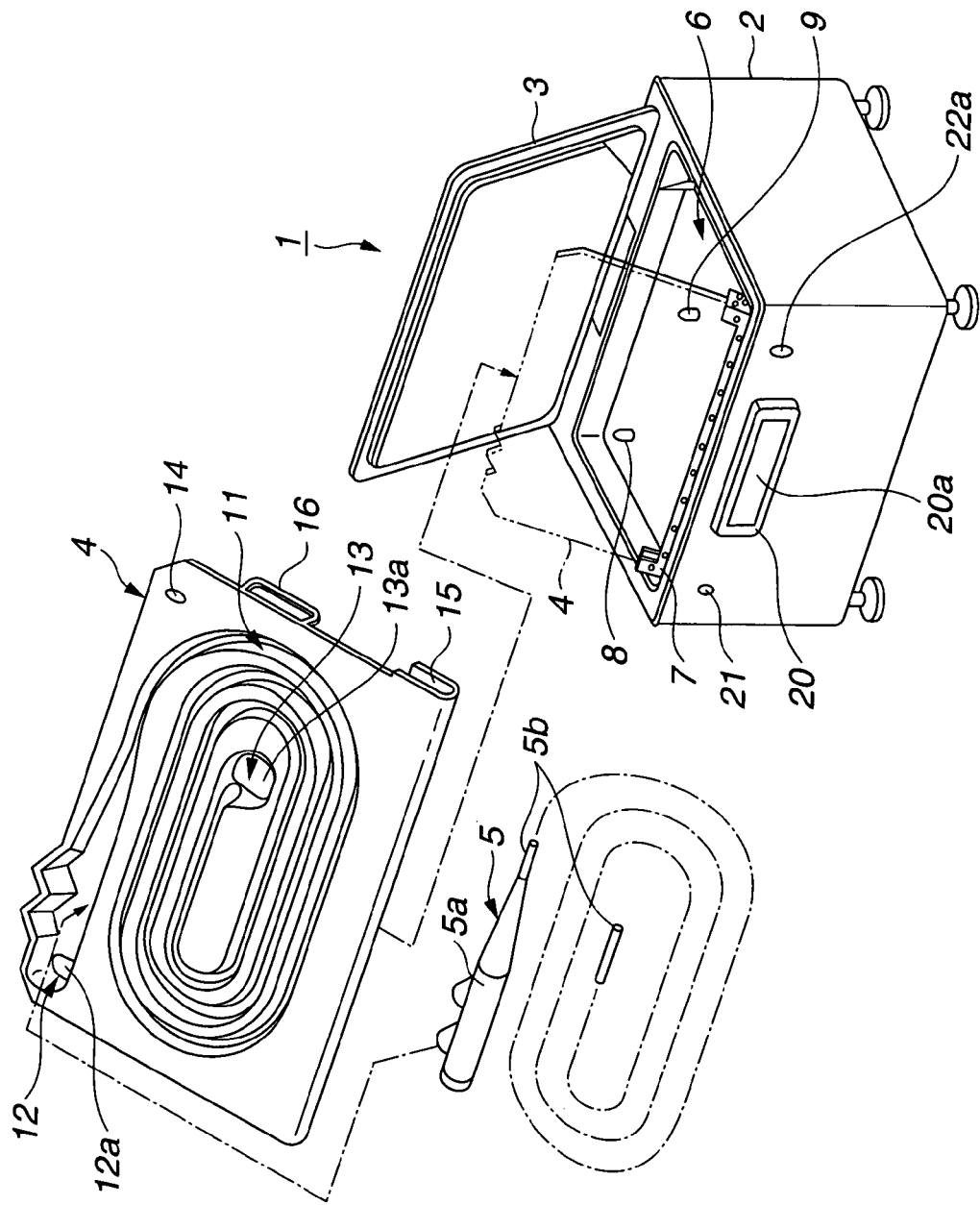
FIG. 1 is a diagram for explaining the relationship between an apparatus body and a tray which stores an endoscope.
Figure 2:
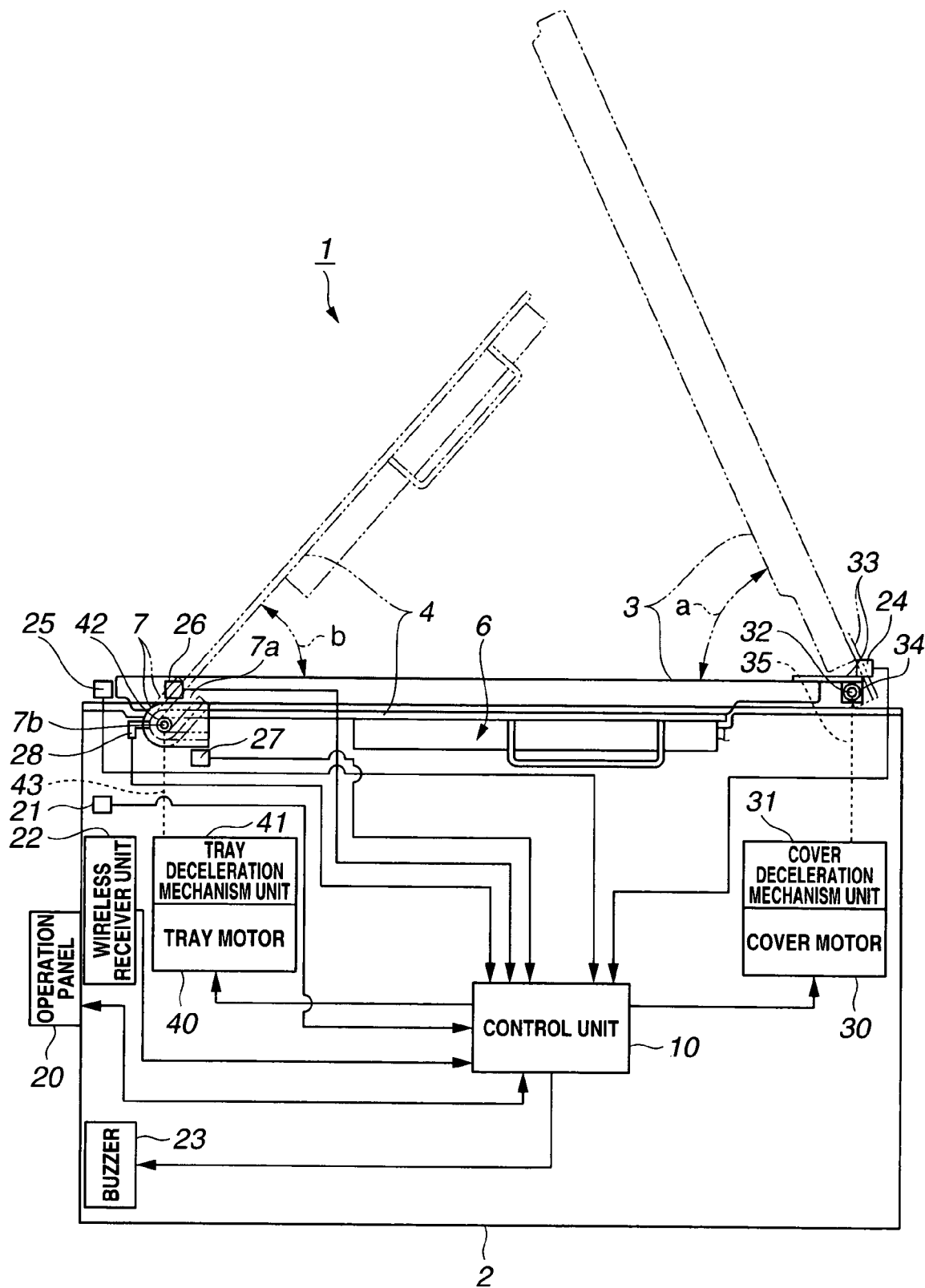
FIG. 2 is a diagram for explaining a configuration and an operation of each of opening/closing mechanisms of a cover and the tray provided to a cleaning/disinfecting apparatus.
Figure 3:
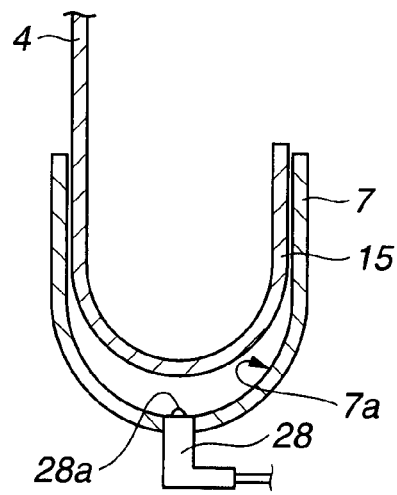
FIG. 3 is a diagram for explaining a state immediately before the setting of the tray in an engagement groove of a tray retaining member.
Figure 4:
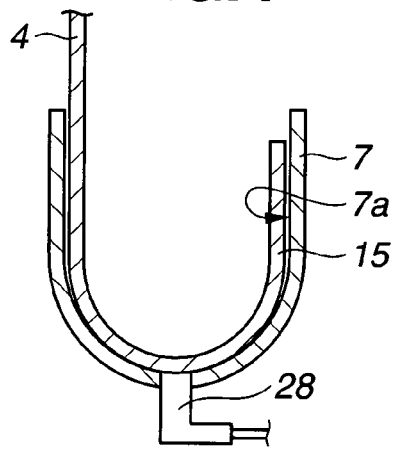
FIG. 4 is a diagram for explaining a state in which the tray is set in the engagement groove of the tray retaining member.
Figure 5:
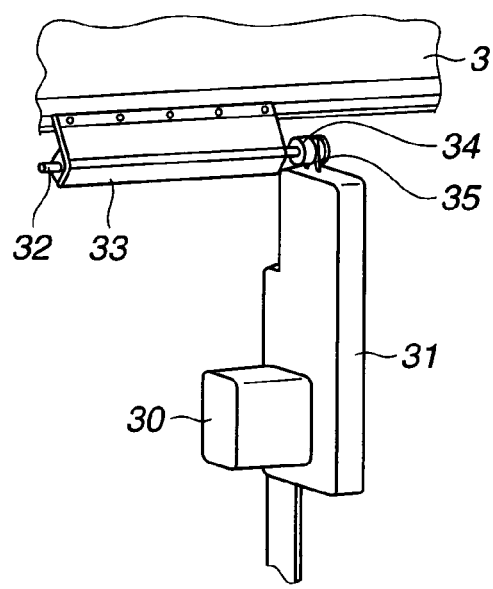
FIG. 5 is a diagram for explaining a configuration example of a cover body opening/closing mechanism unit for causing opening and closing movements of a top cover.
Figure 6:
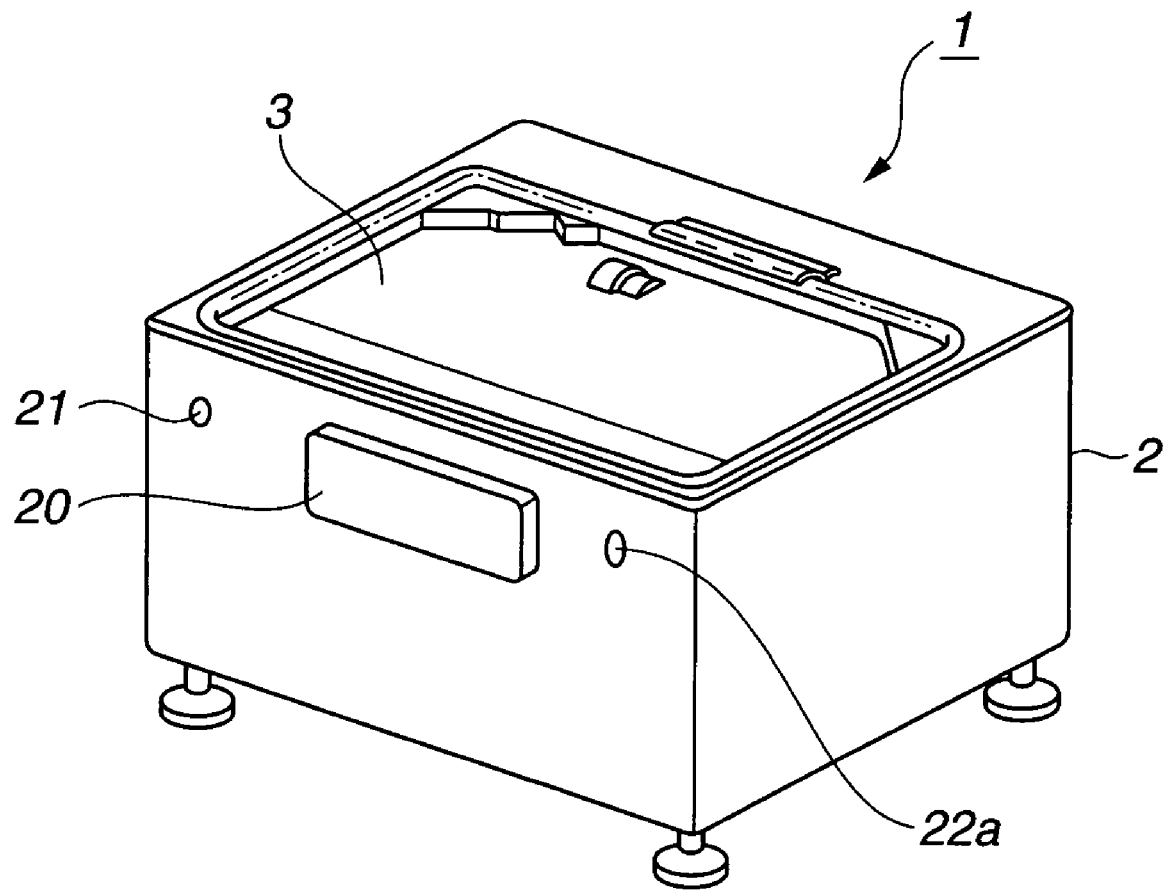
FIG. 6 is a perspective view illustrating the cleaning/disinfecting apparatus in a state in which the top cover is closed.
Figure 7:
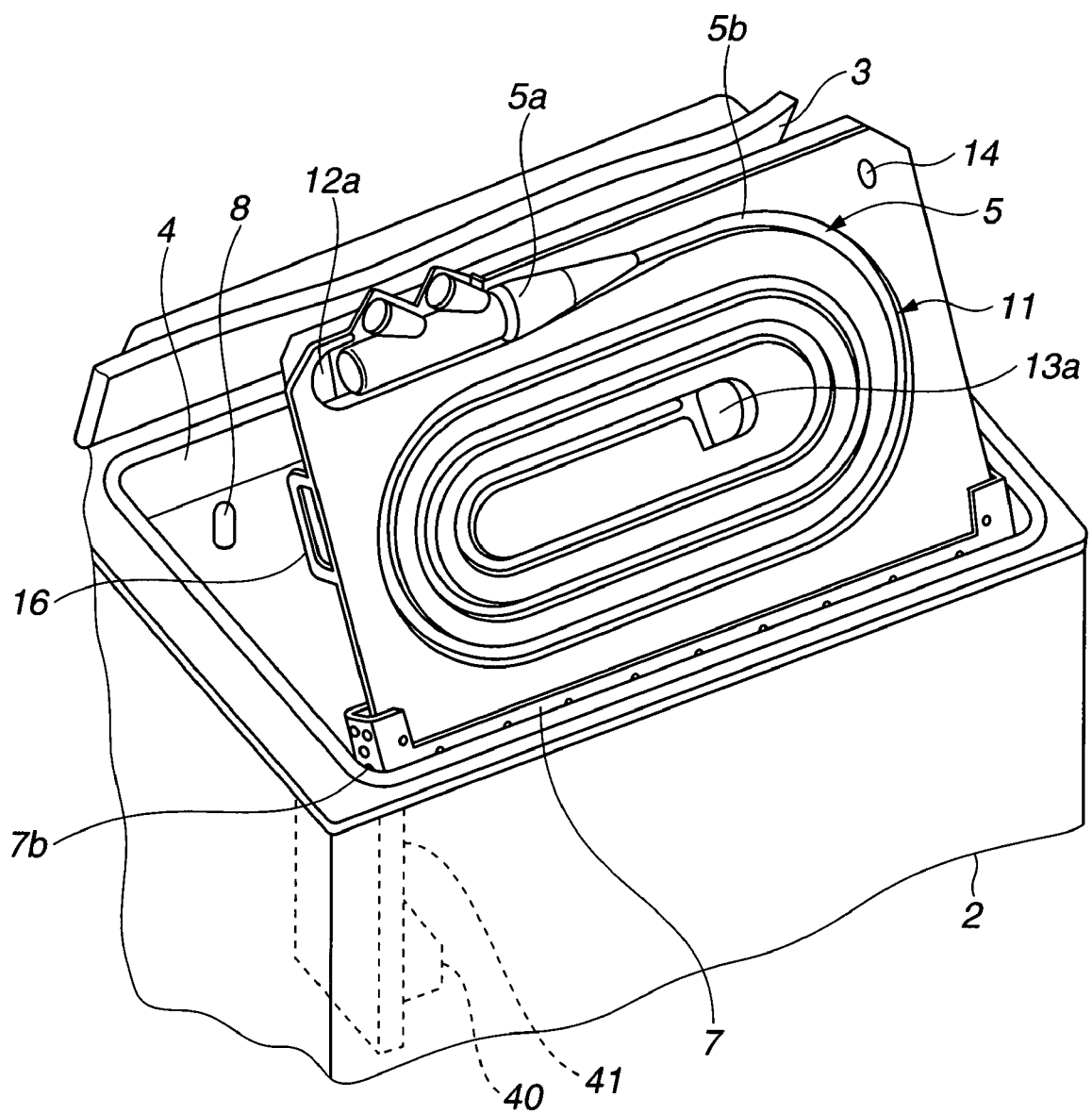
FIG. 7 is a diagram for explaining a configuration example of a tray opening/closing mechanism unit for causing a rotational movement of the tray retaining member, illustrating a state in which the endoscope is stored in the tray retaining member located at a tray attachment/detachment stop position.
Figure 8:
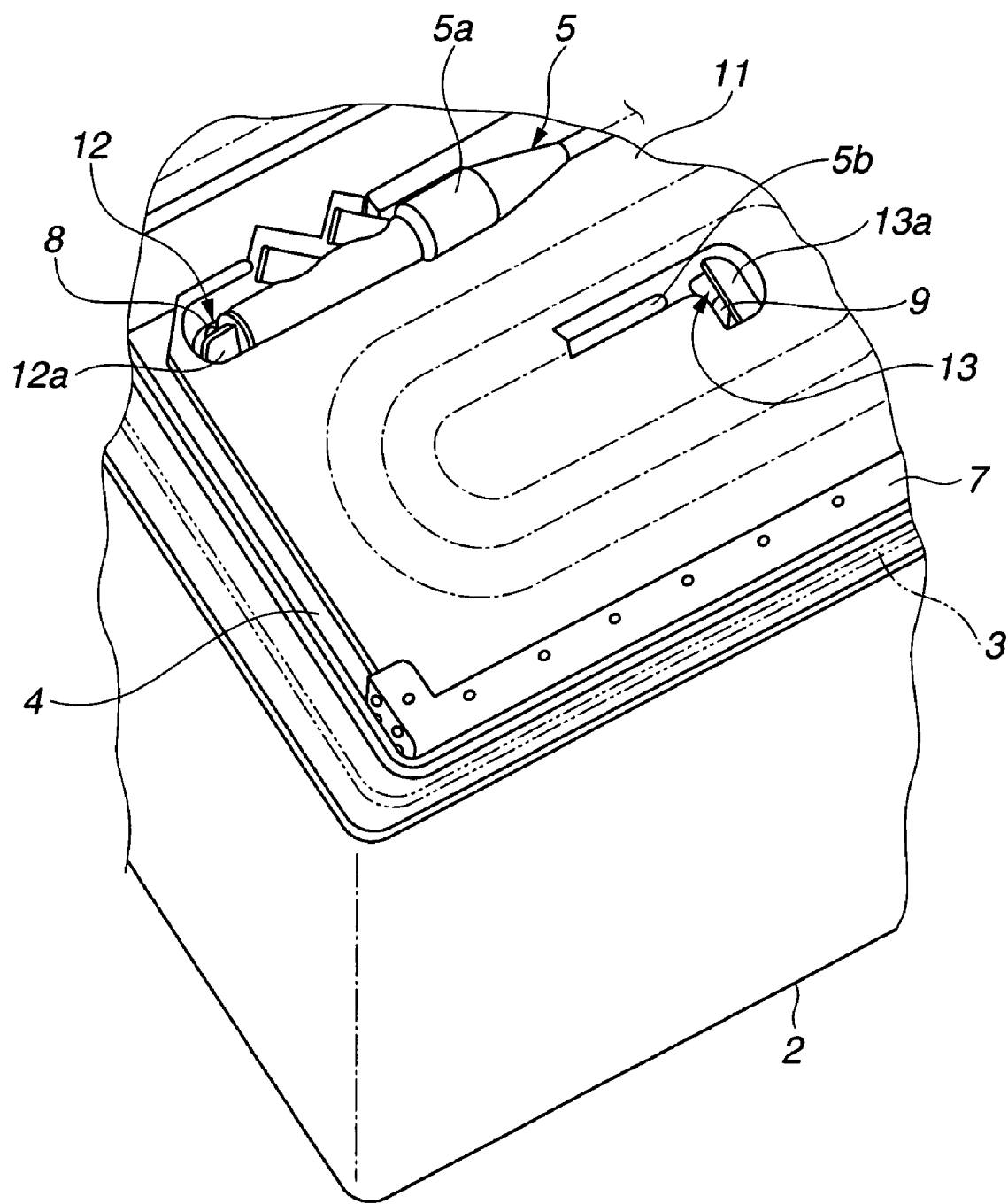
FIG. 8 is a diagram illustrating a state in which the endoscope is stored in the tray retaining member located at a cleaning/disinfection stop position.
Figure 9:
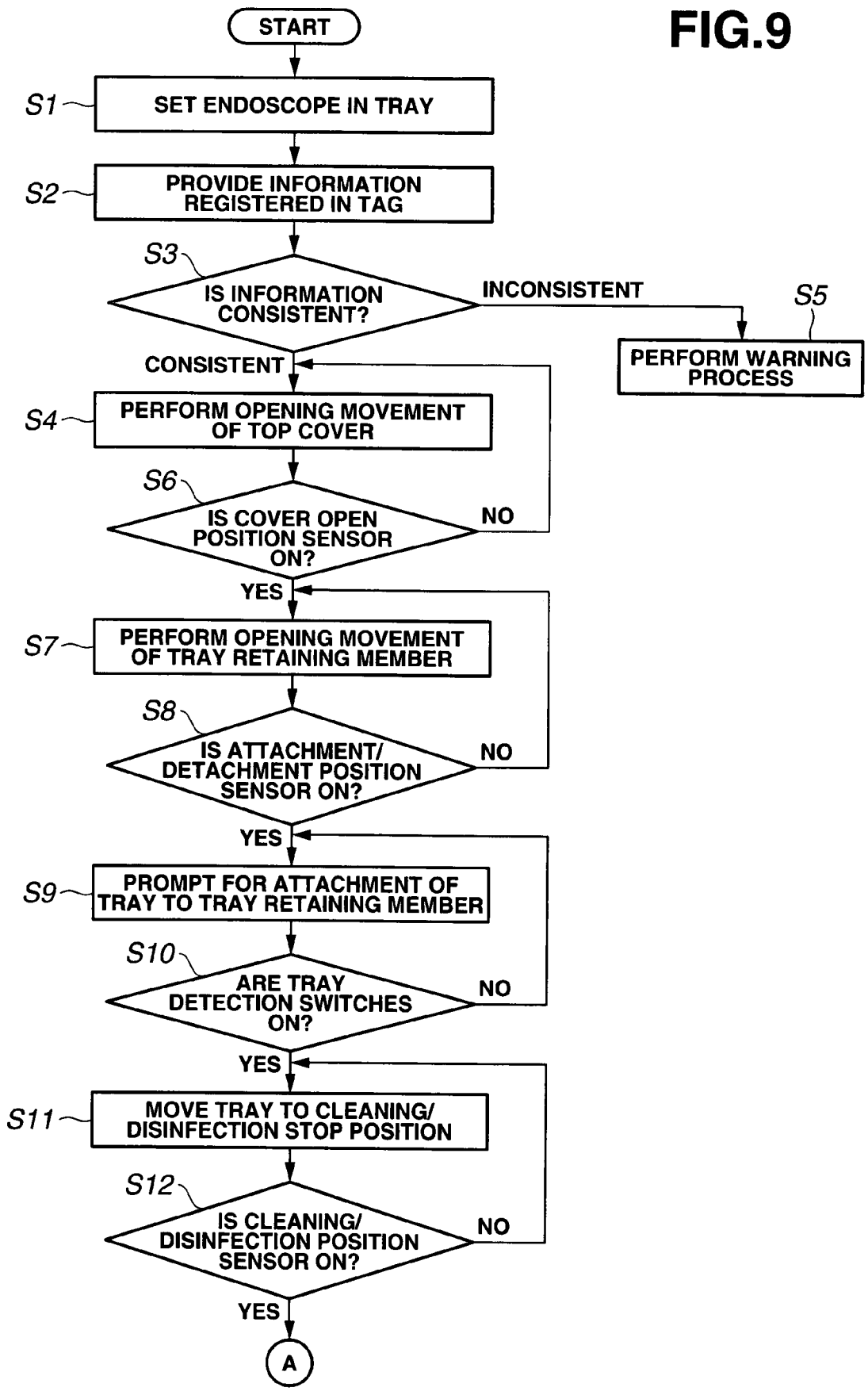
FIG. 9 is a flowchart diagram illustrating the operation of the cleaning/disinfecting apparatus.
Figure 10:
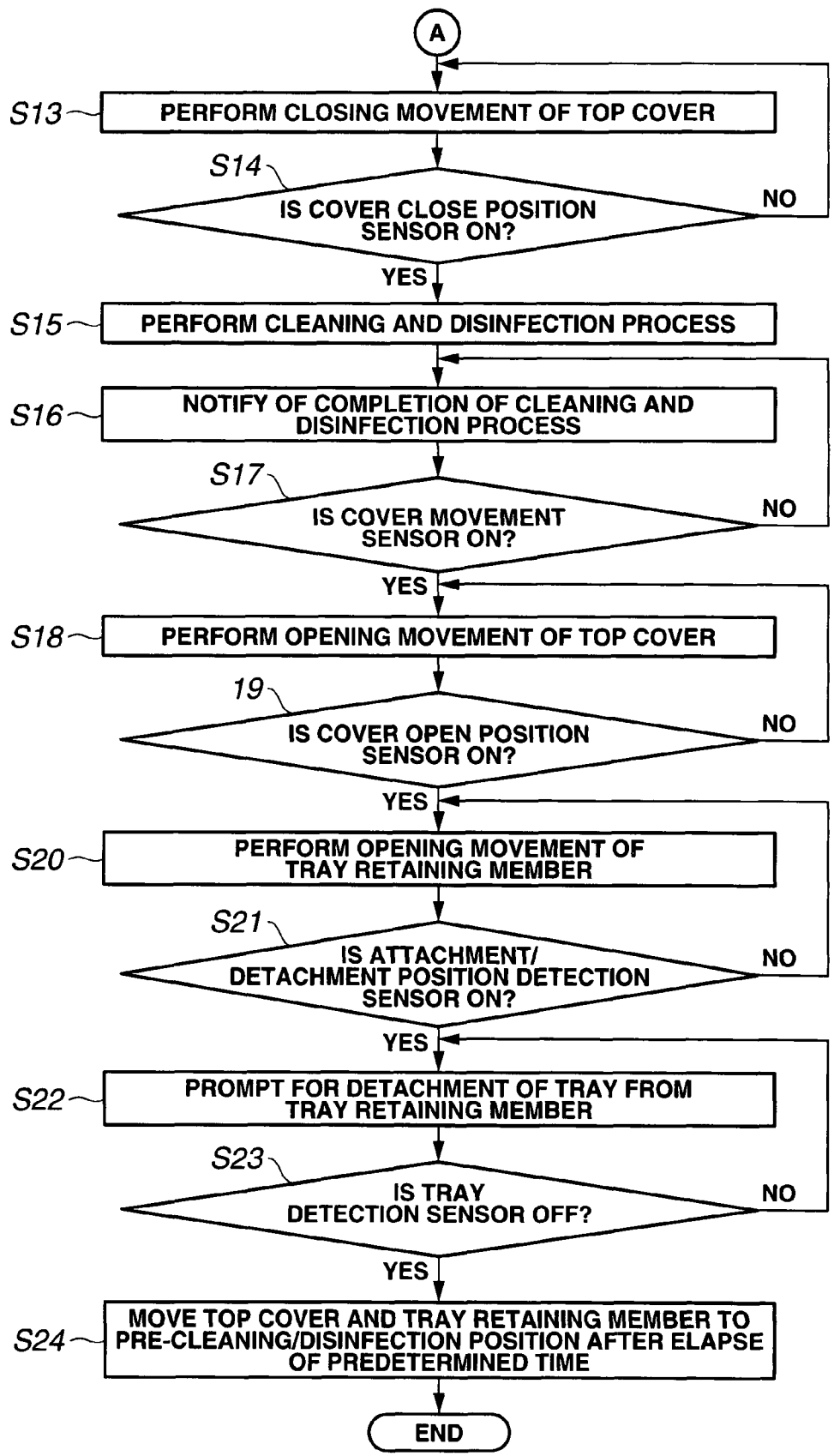
FIG. 10 is a flowchart diagram subsequent to FIG. 9, illustrating the operation of the cleaning/disinfecting apparatus.

FIGS. 1 to 10 relate to an embodiment of the present invention. FIG. 1 is a diagram for explaining the relationship between an apparatus body and a tray which stores an endoscope. FIG. 2 is a diagram for explaining a configuration and an operation of each of opening/closing mechanisms of a cover and the tray provided to a cleaning/disinfecting apparatus. FIG. 3 is a diagram for explaining a state immediately before the setting of the tray in an engagement groove of a tray retaining member. FIG. 4 is a diagram for explaining a state in which the tray is set in the engagement groove of the tray retaining member. FIG. 5 is a diagram for explaining a configuration example of a cover body opening/closing mechanism unit for causing opening and closing movements of a top cover. FIG. 6 is a perspective view illustrating the cleaning/disinfecting apparatus in a state in which the top cover is closed. FIG. 7 is a diagram for explaining a configuration example of a tray opening/closing mechanism unit for causing a rotational movement of the tray retaining member, illustrating a state in which the endoscope is stored in the tray retaining member located at a tray attachment/detachment stop position. FIG. 8 is a diagram illustrating a state in which the endoscope is stored in the tray retaining member located at a cleaning/disinfection stop position. FIG. 9 is a flowchart diagram illustrating the functional operation of the cleaning/disinfecting apparatus. FIG. 10 is a flowchart diagram subsequent to FIG. 9, illustrating the functional operation of the cleaning/disinfecting apparatus.

As illustrated in FIGS. 1 and 2, an endoscope cleaning/disinfecting apparatus 1 is configured to mainly include an apparatus body 2, a top cover 3 forming a cover body openably and closably provided to the apparatus body 2, and an endoscope retaining tray (hereinafter abbreviated as the tray) 4.

A surface of the tray 4, which forms the upper surface of the tray in the drawings, is provided with a storage concave portion 11, which is a concave portion for storing an endoscope 5. The endoscope 5, which is to be subjected to cleaning and disinfection, is configured to include, for example, an operation section 5a and an insertion section 5b which has flexibility and extends from the operation section 5a. The shape of the storage concave portion 11 is designed into a predetermined shape in accordance with the outer shape and the length dimension of the operation section 5a and the insertion section 5b of the endoscope 5 to be stored. That is, the tray 4 is configured as a special type which includes the storage concave portion 11 for storing a predetermined endoscope. Accordingly, a storing operation of storing the used endoscope 5 in the storage concave portion 11 of the tray 4 in a desired state can be easily performed.

In a medical facility having plural types of endoscopes, which are different in the outer shape and the length dimension of the operation section 5a and the insertion section 5b, trays corresponding to the respective types of endoscopes are prepared.

The storage concave portion 11 of the tray 4 is provided with a first fluid supply/discharge port 12 and a second fluid supply/discharge port 13 for supplying and discharging cleaning water, disinfecting water, and so forth to and from the endoscope 5. The first fluid supply/discharge port 12 is disposed in the vicinity of the proximal end side of the operation section 5a of the endoscope 5.

Meanwhile, the second fluid supply/discharge port 13 is disposed in the vicinity of the distal end surface side of the insertion section 5b of the endoscope 5. The respective fluid supply/discharge ports 12 and 13 are provided with openable and closable cover members 12a and 13a, respectively. The cover members 12a and 13a are configured to constantly maintain the fluid supply/discharge ports 12 and 13 in a closed state with the self-weight thereof or with the self-weight thereof and the biasing force of a not-illustrated biasing member.

In the tray 4, therefore, the cover members 12a and 13a are in the closed state in the stand-alone state of the tray. Thus, when the used endoscope 5 is stored in the storage concave portion 11 of the tray 4, dirt, fluid, and so forth adhering to the endoscope 5 are prevented from leaking from the fluid supply/discharge ports 12 and 13. Accordingly, the endoscope 5 can be hygienically carried in the state in which the endoscope 5 is stored in the storage concave portion 11 of the tray 4.

In the present embodiment, cleaning solution, disinfectant solution, and so forth are sent from the first fluid supply/discharge port 12 to the storage concave portion 11. Meanwhile, the cleaning solution, the disinfectant solution, and so forth sent into the storage concave portion 11 is discharged from the second fluid supply/discharge port 13 to a later-described cleaning tank.

The storage concave portion 11 is configured such that, when the cleaning solution, the disinfectant solution, and so forth are sent from the first fluid supply/discharge port 12 to the storage concave portion 11, the disinfectant solution and so forth sufficiently spread over, for example, the outer surface of the operation section 5a and the insertion section 5b of the stored endoscope 5.

At a predetermined position of the tray 4 configured as the special type, e.g., at the right corner of the tray on the upper side of the drawing, a wireless tag (hereinafter abbreviated as the tag) 14 serving as a wireless transmitter unit is mounted. In the tag 14, identification information is registered which indicates, for example, the type of the endoscope stored in the storage concave portion 11 provided in the tray 4. The identification information saved in the tag 14 is, for example, information for determining whether the endoscope is an "upper gastrointestinal endoscope" or a "lower gastrointestinal endoscope," or information for identifying the size of the endoscope, i.e., whether the endoscope is large-sized, middle-sized, or small-sized, for example, from the outer shape and the length dimension of the endoscope.

The tray 4 is provided with an attachment/detachment portion 15 having a U-shape, for example, which is inserted and disposed in an engagement groove 7a of a later-described tray retaining member 7. Further, opposite side portions of the tray 4 are provided with carriage grasping portions 16 grasped by an operator during the carriage of the tray. The carriage grasping portions 16 project from the lower surface of the tray 4 to be prevented from interfering with the top cover 3.

The top cover 3 is formed into a predetermined shape by a rigid, optically-transparent resin member, which is a so-called transparent resin member or semi-transparent resin member. The top cover 3 is openably and closably provided at a predetermined position of the apparatus body 2, and is configured to rotationally move between an open-state stop position indicated by an alternate long and two short dashes line and a closed-state stop position indicated by a solid line, as indicated by an arrow a. The open-state stop position is arbitrarily set in consideration of the operability.

On the upper surface side of the apparatus body 2, a cleaning tank 6 for storing the tray 4 is provided. At a predetermined position in a longitudinal upper surface portion of the apparatus body 2 and on the side of the cleaning tank 6, the tray retaining member 7 is rotatably provided in which the tray 4 is attachably and detachably disposed. The tray retaining member 7 includes the engagement groove 7a which has a bottom surface formed into a substantially U-shape to correspond to the attachment/detachment portion 15, and in which the tray 4 is inserted and disposed.

The tray retaining member 7 is configured to rotationally move between a tray attachment/detachment stop position indicated by an alternate long and two short dashes line and a cleaning/disinfection stop position indicated by a solid line, as indicated by an arrow b. The tray attachment/detachment stop position is set at a predetermined angle, in consideration of the attachment and detachment operability in the attachment and detachment of the tray 4, such that the endoscope 5 stored in the storage concave portion 11 in the tray retaining member 7 held at the tray attachment/detachment stop position is prevented from falling from the storage concave portion 11.

The reference numeral 8 denotes a first cover body opening/closing projection, while the reference numeral 9 denotes a second cover body opening/closing projection 9. The first cover body opening/closing projection 8 and the second cover body opening/closing projection 9 are opening members for pushing the cover members 12a and 13a upward into an open state. Each of the projections is set to have a predetermined height dimension and provided at a predetermined position on the bottom surface of the cleaning tank 6, for example.

The apparatus body 2 is provided with, for example, an operation panel 20, a cover movement instruction sensor 21 serving as a cover body opening instruction detection unit, a wireless receiver unit 22 including a window portion 22a, a buzzer 23 serving as notification means, a cover detection unit for detecting open and close positions of the top cover 3, and a retaining member detection unit for detecting rotational movement positions of the tray retaining member 7. The operation panel 20, the cover movement instruction sensor 21, the wireless receiver unit 22, the buzzer 23, the cover detection unit, and the retaining member detection unit are connected to a later-described control unit 10, which is provided inside the apparatus body 2. On the basis of signals outputted from the respective switches, sensors, and detection units, the control unit 10 performs a variety of controls, such as opening and closing control of the top cover 3, opening and closing control of the tray 4, or control of a cleaning and disinfection process.

The operation panel 20 is provided on, for example, a central upper portion of the front surface, and is provided with switches used to perform a variety of input operations and a display section 20a serving as notification means capable of performing a variety of displays. Information inputted through the switches of the operation panel 20 is registered in a not-illustrated memory unit via the control unit 10. Data registered in the memory unit can be displayed on the display section 20a via the control unit 10 through the operation of the switches of the operation panel 20. The data registered in the memory unit includes such data as data indicating whether the endoscope cleaning/disinfecting apparatus 1 is for the "upper gastrointestinal endoscope" or for the "lower gastrointestinal endoscope," and data of the amount of the cleaning solution to be used, the amount of the disinfectant solution to be used, the cleaning time, the disinfection time, the rinsing time, and so forth, which are determined for each of the endoscope sizes.

The cover movement instruction sensor 21 is provided in, for example, a side portion on the left side of the operation panel 20. In a state in which the display section 20a displays "CLEANING AND DISINFECTION PROCESS COMPLETED," for example, if the operator holds his hand over a position a few centimeters apart from the front surface of the sensor for a predetermined time, the cover movement instruction sensor 21 outputs a tray detachment signal, which is an instruction signal, to the control unit 10.

The window portion 22a of the wireless receiver unit 22 is provided in, for example, a side portion on the right side of the operation panel 20. The wireless receiver portion 22 receives the identification information indicating the type of the endoscope, which is transmitted from the tag 14 mounted on the tray 4. Upon receipt of the identification information transmitted from the tag 14, the wireless receiver unit 22 outputs the identification information transmitted from the tag 14 to the control unit 10 as an endoscope identification signal. The tag 14 may be provided to the endoscope 5 instead of the tray 4.

If the buzzer 23 receives a warning signal outputted from the control unit 10, the buzzer 23 emits an alarm for notifying the operator of abnormality. Meanwhile, if a notification signal is outputted from the control unit 10, the buzzer 23 emits an electronic sound for prompting the operator to proceed to a next operation. If a warning signal is outputted from the control unit 10 to the operation panel 20, the display section 20a displays a later-described warning sentence. If a notification signal is outputted from the control unit 10 to the operation panel 20, the display section 20a displays a later-described notification sentence.

The cover detection unit for detecting the opening and closing positions of the top cover 3 includes a cover open position detection sensor (hereinafter abbreviated as the cover open position sensor) 24 serving as a first cover body position detection unit for detecting the open-state stop position, and a cover close position detection sensor (hereinafter abbreviated as the cover close position sensor) 25 serving as a second cover body position detection unit for detecting the closed-state stop position.

When the top cover 3 is located at the open-state stop position, the cover open position sensor 24 outputs a cover open position signal to the control unit 10. Meanwhile, when the top cover 3 is located at the closed-state stop position, the cover close position sensor 25 outputs a cover close position signal to the control unit 10.

The retaining member detection unit for detecting the rotational movement positions of the tray retaining member 7 includes a tray attachment/detachment position detection sensor (hereinafter abbreviated as the attachment/detachment position sensor) 26 serving as a first tray position detection unit for detecting the tray attachment/detachment stop position, and a cleaning/disinfection stop position sensor (hereinafter abbreviated as the cleaning/disinfection position sensor) 27 serving as a second tray position detection unit for detecting the cleaning/disinfection stop position.

When the tray retaining member 7 is located at the tray attachment/detachment stop position, the attachment/detachment position sensor 26 outputs a tray attachment/detachment position signal to the control unit 10. Meanwhile, when the tray retaining member 7 is located at the cleaning/disinfection stop position, the cleaning/disinfection position sensor 27 outputs a cleaning/disinfection position signal to the control unit 10.

The reference numeral 28 denotes a tray detection switch 28 serving as a tray detection unit. As illustrated in FIGS. 3 and 4, in the present embodiment, a plurality of the tray detection switches 28, for example, are disposed in a bottom portion of the engagement groove 7a of the tray retaining member 7 at predetermined intervals with respect to the longitudinal direction. Each of the tray detection switches 28 is a push-type switch, for example, and includes a projectable and retractable switch portion 28a.

The switch portion 28a is provided to the bottom surface of the engagement groove 7a to project therefrom. Therefore, when the attachment/detachment portion 15 of the tray 4 is inserted into the engagement groove 7a of the tray retaining member 7, as illustrated in FIG. 3, and is disposed in a predetermined disposition state in which the outer surface of the attachment/detachment portion 15 is in close contact with the bottom surface of the engagement groove 7a, as illustrated in FIG. 4, the switch portion 28a is pressed down to output a tray disposition signal to the control unit 10.

The tray detection switch 28 is not limited to the push-type switch, and may be a slide-type switch, an optical sensor, a magnetic detection type reed switch, or the like. Further, the disposition location of the switch is not limited to the tray retaining member 7. Thus, the switch may be provided inside the cleaning tank 6.

Further, the inside of the apparatus body 2 is provided with a variety of tubes, a variety of pumps, a variety of tanks, and so forth, which are not illustrated but used for performing the cleaning and disinfection. Specifically speaking, the variety of tubes include, for example, a tube for supplying or circulating the cleaning water, the cleaning solution, or the disinfectant solution in the tray 4 stored in the cleaning tank 6, a tube for discharging the cleaning water, the cleaning solution, or the disinfectant solution discharged from the second fluid supply/discharge port 13 into the cleaning tank 6, and a tube for supplying, as well as compressed air, alcohol for facilitating the evaporation of residual moisture.

Further, the variety of pumps include, for example, a compressor for sending the compressed air for facilitating a drying operation performed after the cleaning and disinfection, or a pump for sending the cleaning water, the cleaning solution, or the disinfectant solution to the respective tubes described above.

Further, the variety of tanks include, for example, tanks for storing the cleaning solution, the disinfectant solution, or the alcohol described above.

With reference to FIGS. 2 and 5 to 8, description will be made of a configuration of a cover body opening/closing mechanism unit for causing the opening and closing movements of the top cover 3 of the endoscope cleaning/disinfecting apparatus 1, and a configuration of a tray opening/closing mechanism unit for causing the rotational movements of the tray 4.

As illustrated in FIGS. 2 and 5, the cover body opening/closing mechanism unit for causing the opening and closing movements of the top cover 3 is configured to mainly include a cover drive motor (hereinafter abbreviated as the cover motor) 30 provided inside the apparatus body 2, a cover deceleration mechanism unit 31, a rotation shaft 32, and a hinge member 33.

The cover motor 30 is a motor which rotates in the clockwise direction and the counterclockwise direction to cause the top cover 3 to rotationally move from the open-state stop position to the closed-state stop position and from the closed-state stop position to the open-state stop position. The cover deceleration mechanism unit 31 is a mechanism for decelerating the rotation of the cover motor 30 to a predetermined rate to change the opening or closing speed of the top cover 3 to a desired speed.

The cover deceleration mechanism unit 31 is configured to include, for example, a plurality of not-illustrated pulleys and belts. The above-described rotation shaft 32 is disposed parallel to a longitudinal surface of the top cover 3 on the cleaning tank side. One end portion of the rotation shaft 32 is fixed with a pulley 34.

A belt 35 forming the cover deceleration mechanism unit 31 passes over the pulley 34. The hinge member 33 is formed by a plate member having a cross section of an L-shape, for example. The hinge member 33 is integrally fixed to the rotation shaft 32, which projects from opposite side portions of the hinge member 33. Further, the hinge member 33 and an end portion of the top cover 3 on the cleaning tank side are integrally fixed to each other.

When the cover motor 30 is driven, therefore, the rotation of the cover motor 30 is decelerated by the cover deceleration mechanism unit 31, and then is transmitted to the pulley 34 via the belt 35. Thereby, the rotation shaft 32 is rotated. As the rotation shaft 32 starts to rotate, the hinge member 33 integrally fixed to the rotation shaft 32 also rotates along with the rotation of the rotation shaft 32.

The hinge member 33 is integrally fixed to the top cover 3. In the above process, therefore, the top cover 3 is rotationally moved along with the rotation of the hinge member 33, i.e., along with the rotation of the rotation shaft 32.

The rotation direction of the cover motor 30 can be switched on the basis of a drive signal outputted from the control unit 10. If the cover motor 30 is rotated in the clockwise direction (hereinafter described as the forward rotation), for example, under the control of the control unit 10, the top cover 3 is rotationally moved toward the open-state stop position. Meanwhile, if the cover motor 30 is reversely rotated under the control of the control unit 10, the top cover 3 is rotationally moved toward the closed-state stop position.

Further, when the top cover 3 is disposed at the closed-state stop position, as indicated by the solid line in FIG. 2 and as illustrated in FIG. 6, the top cover 3 covers an opening of the cleaning tank 6. At a predetermined position of the top cover 3, a packing (not illustrated) is provided to maintain water tightness. In the cover closed state illustrated in the drawings, the packing is in close contact with the upper surface of the apparatus body 2 to maintain water tightness.

Meanwhile, as illustrated in FIGS. 2 and 7, the tray opening/closing mechanism unit for causing the rotational movements of the tray retaining member 7 is configured to mainly include a tray retaining member rotating motor (hereinafter abbreviated as the tray motor) 40 provided inside the apparatus body 2, and a tray deceleration mechanism unit 41.

The tray motor 40 is a motor for causing the rotational movements of the tray retaining member 7, and rotates in the clockwise direction and the counterclockwise direction. The tray deceleration mechanism unit 41 is a mechanism for decelerating the rotation of the tray motor 40 to a predetermined rate to change the rotational movement speed of the tray retaining member 7 to a desired speed.

The tray deceleration mechanism unit 41 is also configured to include a plurality of not-illustrated pulleys and belts, similarly to the cover deceleration mechanism unit 31. Opposite side portions of the tray retaining member 7 are provided with projections 7b projecting therefrom to serve as a rotation shaft.

A pulley 42 is integrally fixed to one of the projections 7b, and a belt 43 forming the tray deceleration mechanism unit 41 passes over the pulley 42.

When the tray motor 41 is driven, therefore, the rotation of the tray motor 40 is decelerated by the tray deceleration mechanism unit 41, and then is transmitted via the belt 43 to the pulley 42 provided to the projection 7b of the tray retaining member 7. Thereby, the tray retaining member 7 starts to rotationally move.

The rotation direction of the tray motor 40 can be also switched on the basis of a drive signal outputted from the control unit 10. If the tray motor 40 is forwardly rotated, for example, under the control of the control unit 10, the tray retaining member 7 rotationally moves toward the tray attachment/detachment stop position. Meanwhile, if the tray motor 40 is reversely rotated under the control of the control unit 10, the tray retaining member 7 rotationally moves toward the cleaning/disinfection stop position.

Further, when the tray retaining member 7 attached with the tray 4 is disposed at the cleaning/disinfection stop position, as illustrated in FIGS. 2 and 8, the tray 4 is stored in the cleaning tank 6. In such a state, the cover members 12a and 13a provided to the tray 4 are held up by a predetermined amount by the cover body opening/closing projections 8 and 9.

Thus, the fluid supply/discharge ports 12 and 13 are brought into a predetermined open state. Thereby, it is possible to send the cleaning solution, the disinfectant solution, and so forth from the first fluid supply/discharge port 12, and to discharge the cleaning solution, the disinfectant solution, and so forth from the second fluid supply/discharge port 13 into the cleaning tank 6.

Further, in consideration of the manual operation of rotationally moving the top cover 3 and the tray retaining member 7, each of the deceleration mechanism units 31 and 41 may be previously provided with a safety device, such as a torque limiter, to protect the deceleration mechanism units 31 and 41.

With reference to FIGS. 9 and 10, description will be made of the operation of the endoscope cleaning/disinfecting apparatus 1 configured as described above.

The endoscope cleaning/disinfecting apparatus 1 of the present embodiment, which is used in the cleaning and disinfection, is provided with plural types of the trays 4. The trays 4 are stored in a predetermined place in the cleaned and disinfected state. That is, the tray 4 is not disposed in the cleaning tank 6 of the apparatus body 2. In other words, the tray retaining member 7 is not attached with the tray 4.

Further, the top cover 3 provided to the apparatus body 2 is disposed at the closed-state stop position. Furthermore, the endoscope cleaning/disinfecting apparatus 1 is an apparatus for cleaning and disinfecting the upper gastrointestinal endoscope.

To perform the cleaning and disinfection of the used endoscope 5, the operator first prepares the tray 4 corresponding to the endoscope 5, and turns on a main power supply of the apparatus body 2. Then, the control unit 10 confirms the output of the cover close position signal from the cover close position sensor 25 and the output of the cleaning/disinfection position signal from the cleaning/disinfection position sensor 27.

Then, the control unit 10 outputs a notification signal to the operation panel 20 to cause the display section 20a of the operation panel 20 to display a notification sentence, such as "READY FOR CLEANING AND DISINFECTION," to prompt the operator to proceed to the operation.

As described in Step S1, the operator stores the used endoscope 5 in the storage concave portion 11 provided in the tray 4. Thereafter, the operator grasps the carriage grasping portions 16 provided to the tray 4, and carries the tray 4, which stores the endoscope 5, to the apparatus body 2.

Then, to bring the closed top cover 3 provided to the apparatus body 2 into the open state, the identification information registered in the tag 14 is provided, as described in Step S2. To that end, the operator brings the tag 14 provided to the tray 4 close to the window portion 22a provided to the apparatus body 2.

Thereby, the identification information outputted from the tag 14 is received by the wireless receiver unit 22 provided to the apparatus body 2, and the endoscope identification signal corresponding to the identification information is outputted from the wireless receiver unit 22 to the control unit 10.

Upon input of the endoscope identification signal, the control unit 10 compares the endoscope identification signal with the data previously registered in the memory unit, as described in Step S3. In the comparison, if the endoscope identification signal is a signal notifying that the stored endoscope is the "upper gastrointestinal endoscope," the signal is consistent with the data registered in the memory unit. Thus, the result of the comparison is determined as consistent, and the operation shifts to Step S4.

Meanwhile, if the notification signal transmitted from the wireless receiver unit 22 is a signal notifying that the stored endoscope is the "lower gastrointestinal endoscope," the control unit 10 determines that the signal is inconsistent with the data registered in the memory unit. Thus, the operation shifts to a warning process of Step S5.

At Step S5, the control unit 10 outputs a warning signal to the buzzer 23 and the operation panel 20. Thereby, an alarm for warning the operator is emitted from the buzzer 23, while a warning sentence, such as "ENDOSCOPE IS NOT FOR UPPER GASTROINTESTINAL TRACT," is displayed on the display section 20a of the operation panel 20. Accordingly, the operator can immediately realize that the combination of the endoscope cleaning/disinfecting apparatus 1 and the endoscope 5 is incorrect. In the above process, the top cover 3 is held at the closed-state stop position, without being moved open.

At Step S4, the control unit 10 outputs a control signal for causing the cover motor 30 to move the top cover 3 from the closed-state stop position to the open-state stop position. Thereafter, the operation shifts to Step S6. As the control signal is outputted from the control unit 10 to the cover motor 30, the cover motor 30 is forwardly rotated.

Thereby, the top cover 3 starts to rotationally move toward the open-state stop position. Then, along with the movement of the top cover 3, the output of the cover close position signal from the cover close position sensor 25 is stopped. In the above process, the control unit 10 is in a confirmation state in which the control unit 10 confirms whether or not the cover open position signal is outputted from the cover open position sensor 24, as described in Step S6.

Further, the cover motor 30 continues to drive the forward rotation until the control unit 10 confirms the output of the cover open position signal from the cover open position sensor 24.

Upon confirmation of the output of the cover open position signal from the cover open position sensor 24, the control unit 10 performs a control to stop the driving of the cover motor 30. Then, the control unit 10 shifts to Step S7.

As the driving of the cover motor 30 is stopped, the top cover 3 is held at the open-state stop position. Further, instead of the cover close position signal outputted from the cover close position sensor 25, the cover open position signal outputted from the cover open position sensor 24 is confirmed by the control unit 10.

At Step S7, the top cover 3 is held at the open-state stop position. In the step, the control unit 10 outputs a control signal for causing the tray motor 40 to move the tray retaining member 7 from the cleaning/disinfection stop position to the tray attachment/detachment stop position.

Thereafter, the control unit 10 shifts to Step S8. In the process, the tray motor 40 is forwardly rotated due to the output of the control signal from the control unit 10 to the tray motor 40. Thereby, the tray retaining member 7 starts to rotationally move toward the tray attachment/detachment stop position.

Then, along with the movement of the tray retaining member 7, the output of the cleaning/disinfection position signal from the cleaning/disinfection position sensor 27 is stopped. In the above process, the control unit 10 is in a confirmation state in which the control unit 10 confirms whether or not the tray attachment/detachment position signal is outputted from the attachment/detachment position sensor 26, as described in Step S8.

Further, the tray motor 40 continues to drive the forward rotation until the control unit 10 confirms the output of the tray attachment/detachment position signal from the attachment/detachment position sensor 26.

Upon confirmation of the output of the tray attachment/detachment position signal from the attachment/detachment position sensor 26, the control unit 10 performs a control to stop the driving of the tray motor 40. Then, the operation shifts to Step S9.

As the driving of the tray motor 40 is stopped, the tray retaining member 7 is held at the tray attachment/detachment stop position. Therefore, the tray 4 can be attached to the tray retaining member 7. Further, instead of the cleaning/disinfection position signal outputted from the cleaning/disinfection position sensor 27, the tray attachment/detachment position signal outputted from the attachment/detachment position sensor 26 is confirmed by the control unit 10.

At Step S9, the control unit 10 outputs a notification signal to the buzzer 23 and the operation panel 20. Thereby, an electronic sound is emitted from the buzzer 23 to notify the operator that the tray 4 can be attached to the tray retaining member 7.

Meanwhile, the control unit 10 causes the display section 20a of the operation panel 20 to display a notification sentence, such as "ATTACH TRAY," to notify the operator that the operation of attaching the tray can be performed. Then, the operation shifts to Step S10.

At Step S10, the control unit 10 is in a confirmation state in which the control unit 10 confirms whether or not the tray disposition signal has been outputted from all of the tray detection switches 28 provided to the tray retaining member 7.

At Step S9, when the operator is prompted to attach the tray 4 to the tray retaining member 7, the operator inserts the attachment/detachment portion 15 of the grasped tray 4 into the engagement groove 7a of the tray retaining member 7.

In the above process, if the attachment/detachment portion 15 of the tray 4 is disposed in the engagement groove 7a in a predetermined state, as illustrated in FIG. 4, the switch portion 28a of each of the tray detection switches 28 is pressed down. Thereby, the tray disposition signal is outputted from the tray detection switches 28.

If the control unit 10 confirms the output of the tray disposition signal from all of the tray detection switches 28 provided to the tray retaining member 7, the operation shifts to Step S11. In the above process, the tray 4, which stores the endoscope 5 in the storage concave portion 11 thereof, has been attached to the tray retaining member 7, as illustrated in FIG. 7. Further, the control unit 10 confirms the tray disposition signal newly outputted from the tray detection switches 28.

The control unit 10 may be configured to output a warning signal to the buzzer 23 and the operation panel 20 when the control unit 10 confirms the output of the tray disposition signal from some of the tray detection switches 28.

From the alarm emitted from the buzzer 23, the operator can immediately understand that the attachment of the tray 4 to the tray retaining member 7 is insufficient. Meanwhile, from the display of a warning sentence, such as "INSUFFICIENT TRAY ATTACHMENT" on the display section 20a of the operation panel 20, the operator can immediately understand that the attachment of the tray 4 to the tray retaining member 7 is insufficient.

At Step S11, the control unit 10 outputs a control signal for causing the tray motor 40 to move the tray retaining member 7 from the tray attachment/detachment stop position to the cleaning/disinfection stop position. Thereafter, the operation shifts to Step S12. As the control signal is outputted from the control unit 10 to the tray motor 40, the tray motor 40 is reversely rotated.

Thereby, the tray retaining member 7 attached with the tray 4 starts to rotationally move toward the cleaning/disinfection stop position. Then, along with the movement of the tray retaining member 7, the output of the tray attachment/detachment position signal from the attachment/detachment position sensor 26 is stopped.

In the above process, the control unit 10 is in a confirmation state in which the control unit 10 confirms whether or not the cleaning/disinfection position signal is outputted from the cleaning/disinfection position sensor 27, as described in Step S12. Further, the tray motor 40 continues to drive the reverse rotation until the control unit 10 confirms the output of the cleaning/disinfection position signal from the cleaning/disinfection position sensor 27.

Upon confirmation of the output of the cleaning/disinfection position signal from the cleaning/disinfection position sensor 27, the control unit 10 performs a control to stop the driving of the tray motor 40. Then, the operation shifts to Step S13. As the driving of the tray motor 40 is stopped, the tray 4 is stored in the cleaning tank 6, as illustrated in FIG. 8.

In the above process, the first and second cover members 12a and 13a provided to the tray 4 are held up by the cover body opening/closing projections 8 and 9. Thus, the first and second fluid supply/discharge ports 12 and 13 are in the open state. Further, instead of the tray attachment/detachment position signal outputted from the attachment/detachment position sensor 26, the cleaning/disinfection position signal outputted from the cleaning/disinfection position sensor 27 is confirmed by the control unit 10.

At Step S13, the control unit 10 outputs a control signal for causing the cover motor 30 to move the top cover 3 from the open-state stop position to the closed-state stop position. Thereafter, the operation shifts to Step S14. As the control signal is outputted from the control unit 10 to the cover motor 30, the cover motor 30 is reversely rotated. Thereby, the top cover 3 starts to rotationally move toward the closed-state stop position.

Then, along with the movement of the top cover 3, the output of the cover open position signal from the cover open position sensor 24 is stopped. In the above process, the control unit 10 is in a confirmation state in which the control unit 10 confirms whether or not the cover close position signal is outputted from the cover close position sensor 25, as described in Step S14. Further, the cover motor 30 continues to drive the reverse rotation until the control unit 10 confirms the output of the cover close position signal from the cover close position sensor 25.

When the control unit 10 confirms that the cover close position signal has been outputted from the cover close position sensor 25, the control unit 10 performs a control to stop the driving of the cover motor 30. Then, the operation proceeds to the cleaning and disinfection process of Step S15.

As the driving of the cover motor 30 is stopped, the endoscope cleaning/disinfecting apparatus 1 is in a state in which the cleaning and disinfection can be performed, with the top cover 3 held at the closed-state stop position to cover the cleaning tank 6 storing therein the tray 4, as illustrated in FIG. 6. Further, instead of the cover open position signal outputted from the cover open position sensor 24, the cover close position signal outputted from the cover close position sensor 25 is confirmed by the control unit 10.

When the operation shifts to the cleaning and disinfection process of Step S15, the control unit 10 automatically starts a sequence of the cleaning and disinfection process previously registered in the memory unit. The cleaning and disinfection process includes, for example, the cleaning process, the disinfection process, the rinsing process, and so forth.

Upon completion of the cleaning and disinfection process, the control unit 10 shifts to Step S16. At Step S16, the control unit 10 outputs a notification signal to the buzzer 23 and the operation panel 20. Thereby, an electronic sound for prompting the operator to perform a next operation is emitted from the buzzer 23. Meanwhile, the display section 20a of the operation panel 20 displays a notification sentence, such as "CLEANING AND DISINFECTION PROCESS COMPLETED," to prompt the operator to proceed to the operation of detaching the tray. Then, the operation shifts to Step S17.

At Step S17, the control unit 10 is in a confirmation state in which the control unit 10 confirms whether or not the tray detachment signal is outputted from the cover movement instruction sensor 21. When the operator detaches the tray 4, the operator faces the front of the apparatus body 2. Then, for a few seconds, the operator holds his hand or the like in front of the cover movement instruction sensor 21 provided to the apparatus body 2. In the above process, if the control unit 10 confirms the output of the tray detachment signal from the cover movement instruction sensor 21, the operation shifts to Step S18.

If the tray detachment signal is outputted from the cover movement instruction sensor 21 in a state prior to the start of the cleaning and disinfection process or in the cleaning process, i.e., if the tray detachment signal is outputted from the cover movement instruction sensor 21 in other states than the state described in Step S16 in which the completion of the cleaning and disinfection process is notified, the control unit 10 does not output, for example, the control signal for causing the opening movement of the top cover 3.

At Step S18, the control unit 10 outputs a control signal for causing the cover motor 30 to move the top cover 3 from the closed-state stop position to the open-state stop position. Thereafter, the control unit 10 shifts to Step S19. As the control signal is outputted from the control unit 10 to the cover motor 30, the cover motor 30 is forwardly rotated.

Thereby, the top cover 3 starts to rotationally move toward the open-state stop position. Then, along with the movement of the top cover 3, the output of the cover close position signal from the cover close position sensor 25 is stopped. In the above process, the control unit 10 is in a confirmation state in which the control unit 10 confirms whether or not the cover open position signal is outputted from the cover open position sensor 24, as described in Step S19.

Further, the cover motor 30 continues to drive the forward rotation until the control unit 10 confirms the output of the cover open position signal from the cover open position sensor 24.

Upon confirmation of the output of the cover open position signal from the cover open position sensor 24, the control unit 10 performs a control to stop the driving of the cover motor 30. Then, the operation shifts to Step S20. As the driving of the cover motor 30 is stopped, the top cover 3 is held at the open-state stop position. Further, instead of the cover close position signal outputted from the cover close position sensor, the cover open position signal outputted from the cover open position sensor 24 is confirmed by the control unit 10.

At Step S20, the control unit 10 outputs a control signal for causing the tray motor 40 to move the tray retaining member 7 from the cleaning/disinfection stop position to the tray attachment/detachment stop position. Thereafter, the operation shifts to Step S21.

As the control signal is outputted from the control unit 10 to the tray motor 40, the tray motor 40 is forwardly rotated. Then, along with the movement of the tray retaining member 7, the output of the cleaning/disinfection position signal from the cleaning/disinfection position sensor 27 is stopped. In the above process, the control unit 10 is in a confirmation state in which the control unit 10 confirms whether or not the tray attachment/detachment position signal is outputted from the attachment/detachment position sensor 26, as described in Step S21. Further, the tray motor 40 continues to drive the forward rotation until the control unit 10 confirms the output of the tray attachment/detachment position signal from the attachment/detachment position sensor 26.

When the control unit 10 confirms that the tray attachment/detachment position signal has been outputted from the attachment/detachment position sensor 26, the control unit 10 performs a control to stop the driving of the tray motor 40. Then, the operation shifts to Step S22.

As the driving of the tray motor 40 is stopped, the tray retaining member 7 is held at the tray attachment/detachment stop position. Therefore, the operator can detach the tray 4 from the tray retaining member 7. Further, instead of the cleaning/disinfection position signal outputted from the cleaning/disinfection position sensor 27, the tray attachment/detachment position signal outputted from the attachment/detachment position sensor 26 is confirmed by the control unit 10.

At Step S23, the control unit 10 outputs a notification signal to the buzzer 23 and the operation panel 20. Thereby, an electronic sound is emitted from the buzzer 23 to notify the operator that the tray 4 can be detached from the tray retaining member 7. Meanwhile, the control unit 10 causes the display section 20a of the operation panel 20 to display a notification sentence, such as "DETACH TRAY," to notify the operator that the operation of detaching the tray can be performed. Then, the control unit 10 shifts to Step S23.

At Step S23, the control unit 10 is in a confirmation state in which the control unit 10 confirms whether or not the tray disposition signal outputted from all of the tray detection switches 28 provided to the tray retaining member 7 is stopped. At Step S22, when the operator is prompted to detach the tray 4 from the tray retaining member 7, the operator grasps the carriage grasping portions 16 to detach the tray 4 disposed in the tray retaining member 7.

Then, the operator draws the attachment/detachment portion 15 of the tray 4 out of the engagement groove 7a of the tray retaining member 7. Thereby, the switch portion 28a of each of the tray detection switches 28, which has been pressed down by the attachment/detachment portion 15 of the tray 4 as illustrated in FIG. 4, is projected. Then, the output of the tray disposition signal from the tray detection switches 28 is stopped.

The operator carries the tray 4 detached from the tray retaining member 7 to a predetermined location, removes the cleaned and disinfected endoscope 5 from the tray 4, and stores the endoscope 5 in a predetermined place. Meanwhile, at Step S24, after the elapse of a predetermined time since confirmation of the stop of the tray disposition signal outputted from the tray detection switches 28, the control unit 10 outputs a control signal to the tray motor 40 to cause the tray motor 40 to move the tray retaining member 7 to the cleaning/disinfection stop position.

Thereafter, the control unit 10 outputs a control signal to the cover motor 30 to cause the cover motor 30 to move the top cover 3 to the closed-state stop position. Thereby, the apparatus body 2 of the endoscope cleaning/disinfecting apparatus 1 of the present embodiment is brought into a state in which the top cover 3 is closed to the position prior to the start of the cleaning and disinfection.

If the operator wants to dry the inside of the cleaning tank 6, the operator presses a dry mode button (not illustrated) provided to the operation panel 20. Thereby, the top cover 3 is maintained in the open state.

Further, the opening and closing movements of the tray retaining member 7 and the top cover 3 can be reduced in movement time, if the number of the sensors for detecting the respective positions is increased. That is, depending on the detection positions of the increased sensors, it is possible to rotationally move the tray retaining member 7 and the top cover 3 at the same time, while maintaining the positions at which the tray retaining member 7 and the top cover 3 do not interfere with each other. Accordingly, the time taken for the rotational movement of the tray retaining member 7 and the top cover 3 can be reduced.

As described above, according to the endoscope cleaning/disinfecting apparatus 1 of the present embodiment, the special tray 4 is used. Accordingly, it is possible to carry the endoscope 5 while preventing dirt, body fluid, and so forth adhering to the endoscope 5 from dripping from the tray 4 during the carriage of the endoscope 5, and while preventing the hands from becoming unclean.

Further, the endoscope cleaning/disinfecting apparatus 1 is configured such that the tray is provided with the storage concave portion 11 corresponding to the endoscope, and that the storage concave portion 11 is provided with the fluid supply/discharge ports 12, 13 to supply and discharge liquid used in the cleaning and disinfecting operation through the fluid supply/discharge ports 12 and 13. Thus, the cleaning and disinfecting operation can be performed with the supply of an appropriate amount of liquid for the size of the endoscope 5. Accordingly, the processing time and the cost can be reduced.

Further, the endoscope cleaning/disinfecting apparatus 1 is configured to include the tag 14 in which the identification information indicating, for example, the type of the endoscope 5 is registered, and is configured such that the identification information of the tag 14 is wirelessly transmitted to be checked by the control unit of the apparatus body, to thereby cause the top cover of the apparatus body to move from the closed state to the open state on the basis of the result of the check. Accordingly, it is possible to prevent the operational error of incorrectly combining the endoscope 5 with the endoscope cleaning/disinfecting apparatus 1, and to bring the top cover into the open state without touching the apparatus body 2 with a hand.

Further, with the use of the buzzer 23 and the display section 20a, the endoscope cleaning/disinfecting apparatus 1 of the present embodiment auditorily and visually warns the operator of a problem occurring during an operation and performs notification for prompting the operator to proceed to a next operation. Accordingly, the cleaning and disinfecting operation can be improved in efficiency.

According to the above-described features, the operator can promptly perform the setting and the detachment of the used endoscope 5 with respect to the storage concave portion 11. Further, the carriage of the endoscope 5 and the attachment and the detachment of the tray 4 can be effectively and hygienically performed. Furthermore, the cleaning and disinfecting operation of the used endoscope 5 can be effectively and hygienically performed.

In the present embodiment, the identification information registered in the tag 14 is the information for checking whether the endoscope 5 is the "upper gastrointestinal endoscope" or the "lower gastrointestinal endoscope." However, the identification information is not limited to the above, and may be identification information for checking the size of the endoscope 5. Accordingly, cleaning and disinfection patterns according to the type of the endoscope 5, which are varied in the amount of chemical solution used in the cleaning and the disinfection, the cleaning time, the disinfection time, and so forth, are previously registered in the memory unit. It is therefore possible to effectively perform the cleaning and disinfection at low cost and in short time, by determining the endoscope size from the identification information obtained from the tag and then setting the cleaning and disinfection pattern corresponding to the endoscope 5.

The present invention is not limited only to the above-described embodiment, and can be modified in various ways within a scope not departing from the gist of the invention.

The invention claimed is:

1. An endoscope cleaning/disinfecting apparatus comprising:
    an apparatus body including a cleaning tank for storing an endoscope retaining tray in which an endoscope is stored;
    a cover body provided to the apparatus body, and caused by a cover body opening/closing mechanism unit to rotationally move between an open-state stop position and a closed-state stop position;
    a wireless transmitter unit provided to either one of the endoscope retaining tray and the endoscope stored in the endoscope retaining tray, and transmitting information for identifying the type of the endoscope;
    a wireless receiver unit provided to the apparatus body, and receiving the information of the wireless transmitter unit;
    a memory unit provided to the apparatus body, and previously storing information on the type of the endoscope to which the endoscope cleaning/disinfecting apparatus is applicable; and
    a control unit provided to the apparatus body, and controlling an opening operation of the cover body opening/closing mechanism unit so as to cause an opening movement of the cover body, when the information obtained by the wireless receiver unit is consistent with the information stored in the memory unit.

2. The endoscope cleaning/disinfecting apparatus according to claim 1, wherein the apparatus body further includes a tray retaining member to which the endoscope retaining tray can be attachably and detachably attached, and a tray retaining member rotating mechanism unit for causing the tray retaining member to rotationally move between a tray attachment/detachment stop position and a cleaning/disinfection stop position under the control of the control unit.

3. The endoscope cleaning/disinfecting apparatus according to claim 2, wherein the tray retaining member further includes a tray detection unit, and the apparatus body further includes a first cover body position detection unit for detecting the open-state stop position of the cover body, a second cover body position detection unit for detecting the closed-state stop position of the cover body, a first tray position detection unit for detecting the tray attachment/detachment stop position of the tray retaining member, a second tray position detection unit for detecting the cleaning/disinfection stop position of the tray retaining member, and notification means for warning or notifying an operator of an operation state in at least one of a visual manner and an auditory manner.

4. The endoscope cleaning/disinfecting apparatus according to claim 3, wherein the apparatus body further includes a cover body opening instruction detection unit for outputting, after the completion of a cleaning and disinfection process, an instruction signal for causing the control unit to output a control signal for causing the cover body opening/closing mechanism unit to rotationally move the cover body from the closed-state stop position to the open-state stop position.

5. The endoscope cleaning/disinfecting apparatus according to claim 1, wherein the endoscope retaining tray includes a storage concave portion corresponding to the outer shape and the length dimension of the endoscope stored therein, fluid supply/discharge ports provided to the storage concave portion in the vicinity of a proximal end portion of an operation section and in the vicinity of a distal end portion of an insertion section, respectively, and cover members for closing the respective fluid supply/discharge ports.

6. The endoscope cleaning/disinfecting apparatus according to claim 5, wherein the apparatus body includes opening members for bringing the cover members, which closes the fluid supply/discharge ports, into an open state.

\* \* \* \* \*